United States Patent [19]
Gray et al.

[11] Patent Number: 6,122,846
[45] Date of Patent: Sep. 26, 2000

[54] FORCE MONITORING SHOE

[75] Inventors: Frank B. Gray, 5104 Lionsview Dr., Knoxville, Tenn. 37919; John L. Parris, Knoxville, Tenn.; David H. Gray, Knoxville, Tenn.; Raimer G. Riffert, Knoxville, Tenn.

[73] Assignee: Frank B. Gray, Knoxville, Tenn.

[21] Appl. No.: 09/385,393

[22] Filed: Aug. 30, 1999

[51] Int. Cl.[7] ...................................................... A61B 5/11
[52] U.S. Cl. ................................ 36/136; 36/137; 36/139; 600/592; 73/172; 340/573
[58] Field of Search .............................. 36/136, 132, 137, 36/139; 600/592; 73/172; 340/573

[56] References Cited

U.S. PATENT DOCUMENTS

| | | | |
|---|---|---|---|
| 5,269,081 | 12/1993 | Gray | 36/136 |
| 5,357,696 | 10/1994 | Gray et al. | 36/136 |
| 5,673,500 | 10/1997 | Huang | 36/136 |

*Primary Examiner*—Paul T. Sewell
*Assistant Examiner*—Troy Arnold
*Attorney, Agent, or Firm*—Pitts & Brittian, P.C.

[57] ABSTRACT

An apparatus and method of operation for measuring forces applied to a wearer's foot, the apparatus providing an indication to the wearer when forces on the foot exceed pre-selected upper limits or do not meet pre-selected lower limits. A body member is disclosed for attachment around the wearer's foot, the body member having an exterior sole and an interior sole portion covered by a rigid foot plate. The foot plate includes an upper support surface for contact with the foot. The interior sole portion includes at least one cavity within, with a force sensing unit attachable partially within the cavity. At least one strain gage is positioned at a midpoint on the force sensing unit, and the force sensing unit is connectable to the underside of the foot plate. An electronic means is mounted within the cavity and is electrically connected to the at least one strain gage. The electronic means receives electronic signals from the strain gage, the signals in proportion to force applied onto the force sensing unit when the wearer's foot applies weight onto the foot plate, with conversion of the signals to output signals for transmission to a signal processing means in a remotely located receiver and display unit. The display unit compares the output signals to upper limits and lower limits, and displays alarms when output signals do not reach lower limits, or exceed upper limits, therefore assisting with therapeutic rehabilitation of an injured lower extremity.

20 Claims, 8 Drawing Sheets

FORCE MONITORING SHOE

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF INVENTION

1. Field of Invention

The present invention relates generally to the field of force monitoring systems and more particularly to a force monitoring system for use in an orthopedic shoe capable of limb load monitoring of forces placed onto a force sensing shoe insert.

2. Description of the Related Art

In the field of force monitoring for orthopedic use, shoe insert devices are available that monitor weight applied onto a limb, with computer analysis available for analyzing weight measurements and triggering alarms depending on the weight and load boundaries programmed into the computer software.

In U.S. Pat. No. 5,269,081, to Gray, a force monitoring shoe is disclosed for monitoring the force applied to a patient's leg, as monitored by a force absorption scheme including a heel platform, and a vibration generator located underneath the middle portion of the user's foot, a force monitoring device, and a signaling system. The force monitoring device senses the applied force on the absorption scheme and compares the forces monitored with desired, pre-selected limits, for feedback signaling to the user.

In U.S. Pat. No. 5,253,654, to Thomas et al., an orthopedic weight monitor is disclosed for detecting the forces imposed on the heel of the foot. The weight monitor includes a flexible pad placed inside a shoe in the heel area, with a thin rigid plate having a foil strain gage underneath the plate and within the pad, with an electronic module attached by electrical wires to the strain gage. The strain gage determines weight bearing values for the heel, and the electronic module issues a warning for weight values exceeding a predetermined limit.

In U.S. Pat. No. 5,323,650, to Fullen et al., a force sensor array is disclosed that is positioned within a user's shoe between the foot and the inner sole of the shoe, with the force sensor array having a multiplicity of individual force sensors. Electronic scanning circuitry is connectable to the force sensor array for indicating the instantaneous force sensed by each of the multiplicity of individual force sensors to allow processing of information to obtain and store force data from the force sensor array.

In U.S. Pat. No. 5,357,696, to Gray et al., an orthopedic device is disclosed for monitoring force applied to a wearer's foot. The shoe insert device includes a pressure sensitive element that produces an electrical signal that is related to the force applied by the wearer's foot. The pressure sensitive element is sandwiched between resilient members that are positioned under the central area of the shoe insert. A feedback signaling device receives electrical signals from the pressure sensitive element, with the signaling device including a electronic circuit module for alerting the user of excessive weight applied to the force sensor array.

Prior shoe insert devices include pads that absorb and monitor forces on specific rear areas and/or front areas of a user's foot, with total downward forces calculated from the weight transferred to the rear areas, or front areas of a user's foot. Prior shoe insert devices do not provide an orthopedic shoe that monitors the differences in weight distribution across a shoe insert foot plate, with resulting measuring of strain created between the rear of a foot plate and the front of the foot plate, with adjustable structures provided within the shoe insert to minimize strain resulting from shoe flex and lateral forces generated by the user's foot. Therefore true force readings for the weight bearing surfaces of the user's foot may not be adequately measured by prior devices.

Accordingly, there is a need for an improved force monitoring system for use in an orthopedic shoe having a shoe insertable force sensing unit that is capable of measuring downward forces imposed by a wearer's weight distribution onto the foot of an injured limb, and capable of measuring the resultant downward forces occurring at any place over the length of the wearer's foot.

Therefore, it is an object of the present invention to provide an improved force monitoring system for monitoring weight applied to a person's foot for diagnosing, training, and healing purposes.

It is another object of the present invention to provide an improved force monitoring system that is incorporated into an orthopedic shoe and includes visual, audible, and/or vibration notification to the wearer of the force monitoring system.

It is another object of the present invention to provide a force monitoring system that includes a force sensing unit that monitors weight imposed at any point along the length of a wearer's foot within an orthopedic shoe.

It is another object of the present invention to provide a force monitoring system that measures weight imposed on a wearer's foot for each step and reports to the wearer any weight imposed on the wearer's foot exceeding pre-selected upper limits, or weights below pre-selected lower limits.

BRIEF SUMMARY OF INVENTION

In accordance with the present invention, an improved force monitoring system for use in an orthopedic shoe is disclosed that provides an orthopedic device for monitoring and alerting the wearer of forces subjected to a wearer's foot that exceeds a pre-set range of forces. The apparatus includes a force sensing unit comprising a force sensing beam with at least one strain gage attached thereon, a foot plate covering the beam, the foot plate having an upper surface for contact with the foot of the wearer, and a lower surface connectable to the force sensing beam. The force monitoring system includes a sole portion having an upper surface with at least one cavity therein, the upper surface attachable to the ends of the force sensing beam that is insertable into the cavity, and the sole portion having a lower surface for contact with a supporting surface. A beam control circuitry module including electronic circuitry is mountable within the cavity and is electrically connected to a strain gage attached on the force sensing beam. The electronic circuitry receives signals from the strain gage and converts the strain gage analog signals to digital output signals for remote transmission to a receiver and display unit having a processing means at a remote location. The received output signals are analyzed and compared to pre-selected upper weight limits, or pre-selected lower weight limits. The receiver and display unit displays the numerical weights imposed by the foot of the wearer that lie between the lower and upper weight limits and that exceed the upper weight limits, and displays alarm lights when lower weight limits are not met. No numerical weight value is displayed for weights measured below the pre-selected lower weight limit. The benefits provided by the force monitoring shoe include protection of the affected extremity during the healing process, training of the wearer for rehabilitation, documentation of compliance or non-compliance with a prescribed weight-bearing training program, and accurate assessment of the specific weight applied to an extremity during each step, and/or applied over a multitude of steps.

BRIEF DESCRIPTION OF SEVERAL VIEWS OF THE DRAWINGS

The above mentioned objects and advantages of the present invention are readily apparent from the following description contained herein, and by reference to the claims, read together with the drawings in which:

FIG. 5a is a top view of a front beam support connector of the force sensing unit;

FIG. 5b is a bottom view of the front beam support connector of FIG. 5a;

FIG. 6a is a top view of a front foot plate pivotable support of the force sensing unit;

FIG. 6b is a bottom view of the front foot plate pivotable support of FIG. 6a;

FIG. 7a is a top view of a rear foot plate pivotable support of the force sensing unit;

FIG. 7b is a bottom view of the rear foot plate pivotable support of FIG. 7a;

FIG. 8a is a top view of a rear beam support connector attachable at the heel area of the force sensing unit;

FIG. 8b is a bottom view of the rear beam support connector of FIG. 8a;

DETAILED DESCRIPTION OF INVENTION

An improved force monitoring system incorporating a force monitoring apparatus within an orthopedic shoe including various features of the present invention is illustrated generally as a force monitoring shoe 10 in the FIGS. 1–12. The force monitoring shoe 10 is designed to provide an orthopedic shoe (see FIG. 1), for measuring force applied to a foot of a wearer, the device providing an indication to the wearer when the force is below or exceeds pre-selected limits, as determined by the wearer or a medical therapist working with the wearer during rehabilitation of an injured lower extremity. A typical wearer of the force monitoring apparatus can be people who have undergone soft tissue or skeletal trauma to a lower extremity, or any other surgical procedure such as hip repair or replacement, knee repair, or ankle repair. The force monitoring apparatus provides instantaneous force readings to a wearer to allow the wearer to reduce the weight on the foot, therefore lessening the force transmitted to the healing lower extremity, or to notify the wearer to increase the weight on the foot, to keep the patient's weight within a range of preferred weight during walking for therapeutic purposes.

Figures 1, 1A:
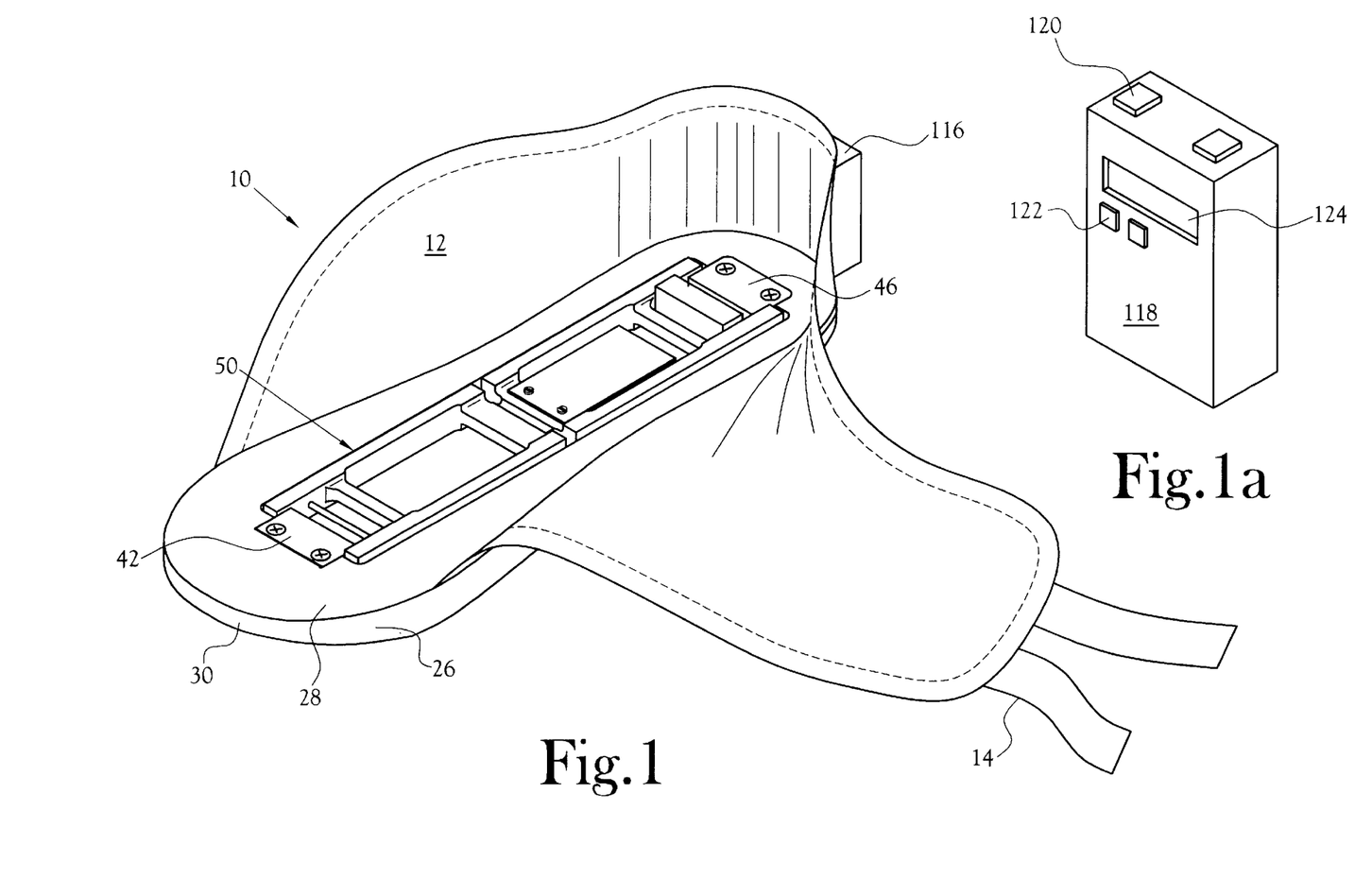
FIG. 1 is a perspective view of a force sensing unit within a force monitoring shoe of the present invention.
FIG. 1a is a perspective view of a receiver and display unit for use with the force monitoring shoe of the present invention.

Specifically, the force monitoring shoe 10 includes an orthopedic shoe enclosure configuration 12 for enclosing the foot of a wearer. The enclosure 12 may be a shoe specifically designed for ease of entry and exit, as shown in FIG. 1, or may be an athletic shoe having modifications to accommodate the force sensing unit 50 described below. If enclosure 12 is utilized, the enclosure includes an upper body member attachment means 14 that can include velcro straps and/or buckles for securing the enclosure 12 onto the foot. The enclosure 12 can include a battery pack 116 located on the exterior of enclosure 12 (FIG. 1).

Figure 2:
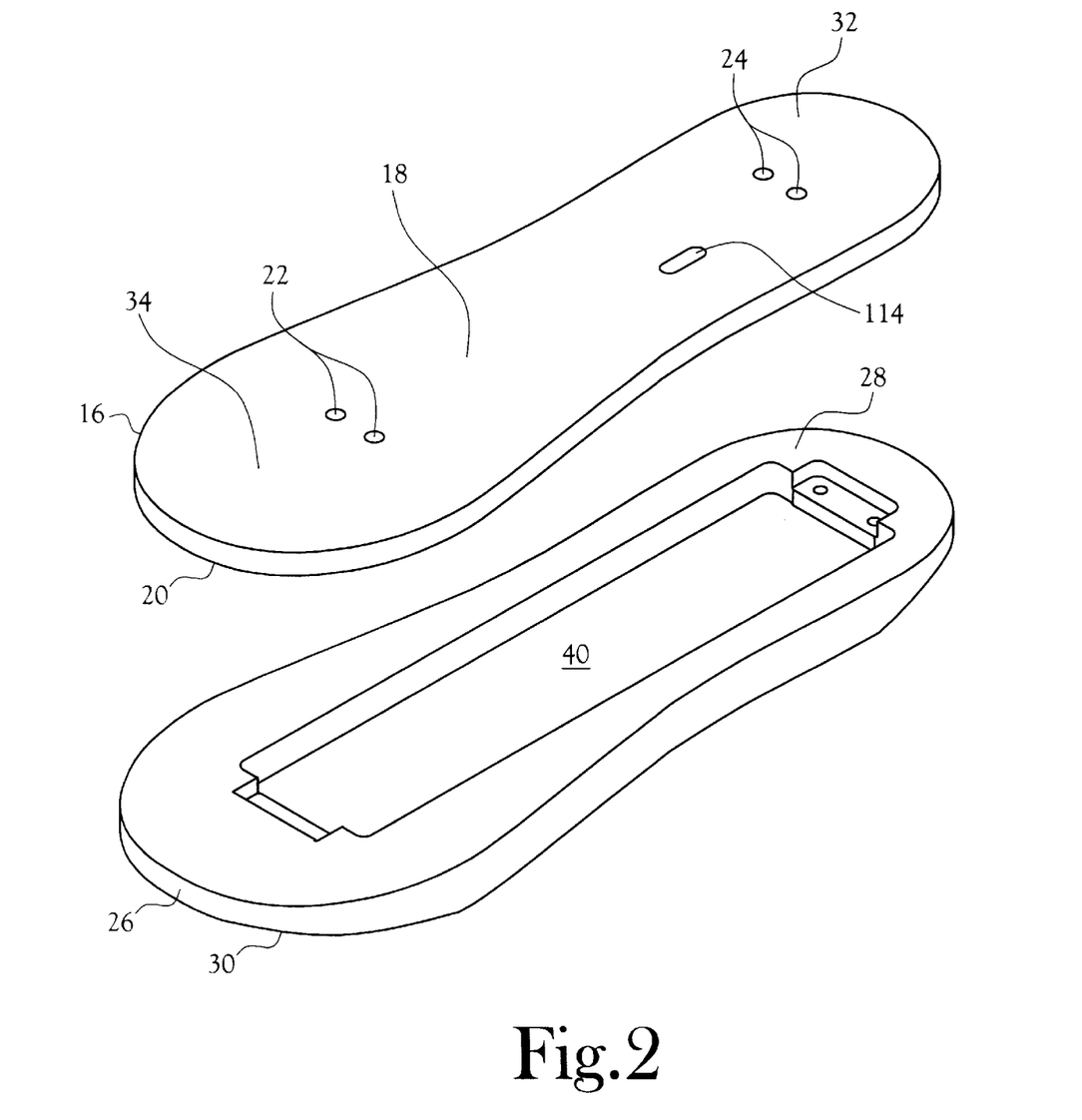
FIG. 2 is an exploded perspective view of a foot plate, sole, and cavity of the force monitoring shoe of FIG. 1.
Figure 10:
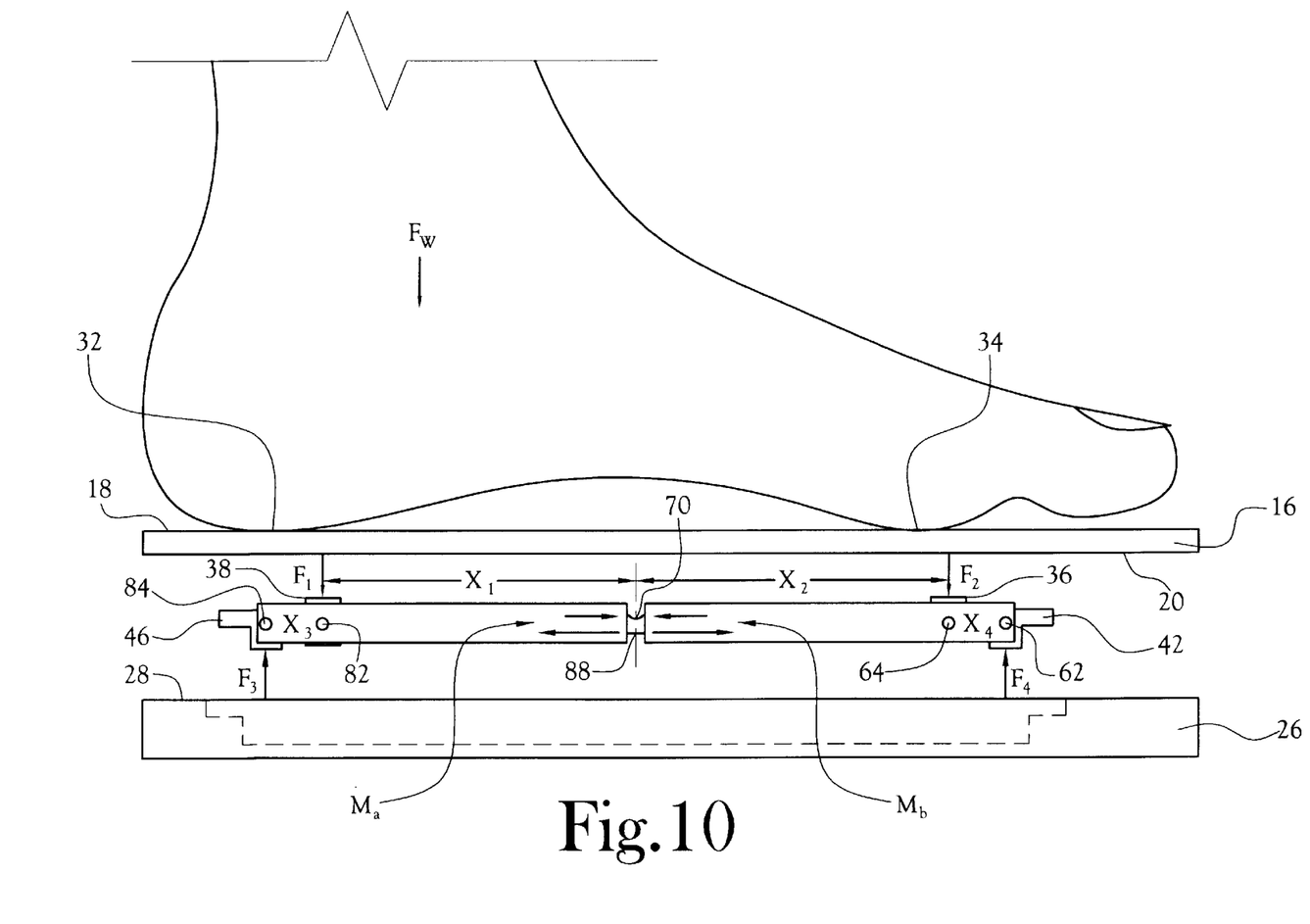
FIG. 10 is a side view of the assembled force sensing unit illustrating the central groove, and the forces subjected to the force sensing unit by a wearer's foot.

The force monitoring shoe 10 includes a generally rigid layer supporting the foot within the body member enclosure 12, including an insertable interior foot plate 16 for support of the foot of a wearer, with the foot plate 16 having an upper surface 18 for contact with the foot, and an underside surface 20 for contact with the foot plate front support 36 and rear support 38 (see FIGS. 2 and 10). The foot plate 16 includes a pair of front attachment holes 22 at the forefoot area of the plate 16, and a pair of rear attachment holes 24 at the heel area of the plate 16. The plate 16 is made of rigid material such as rigid metal, rigid plastic, wood, and/or other rigid material that does not twist or bend when force from placement of a wearer's partial weight is applied anywhere along the length of the foot plate 16, as on the heel area 32 during the heel-strike motion of walking, or as applied at the forefoot area 34 during the forefoot push-off motion of walking. The lower sole portion 26 (see FIGS. 1 and 2), includes a lower surface 30 of the sole for contact with a supporting surface such as a floor or a treadmill. The upper surface 28 houses a generally rectangular cavity 40 within a central area of the upper surface 28 of the sole. The foot plate 16 fits over the upper surface 28, covering the cavity 40 during use and operation of the force monitoring shoe 10.

Within the cavity 40 and underneath the forefoot area 34 of the foot plate 16, is positioned a front beam support connector 42 (see FIGS. 3, 5a and 5b), that is removably attachable to the upper surface 28 of sole 26 (FIG. 1). The front beam support connector 42 slips onto a front cross-pin 62 spanning the front portion of a beam 52 of a force sensing unit 50 (See FIGS. 3 and 4, and as discussed below). The front beam support connector 42 includes a rearward facing slot 44 that accepts the front cross-pin 62, and provides a slidable interface between the front beam support connector 42 and the front portion of beam 52 with the inserted front beam cross-pin 62 inserting into slot 44. Rear beam support connector 46 is attachable by screws or bolts (not shown) to rear attachment holes in the rear portion of cavity 40.

The rear portion of beam 52 fits into cavity 40 underneath the heel area 32 of the foot plate 16 (see FIGS. 3, 4, 8a and 8b). The rear portion of beam 52 is attached to a rear beam support connector 46 that includes a horizontally oriented, interior bore 48 that accepts therethrough a fourth or rear cross-pin 84 that spans the rear portion of beam 52. Pivoting of the rear beam support 46 connector around the rear cross-pin 84 allows the rear beam support 46 to shift slightly as the connected beam 52 shifts slightly horizontally when weight is transferred across the foot plate 16, as the wearer's foot imparts force onto the foot plate 16 during the normal walking motion that can force the shoe 10 to flex slightly with transfer of weight from the heel to the forefoot during a patient's steps.

Foot plate front support 36 is rotatable around beam pin 64 that spans the beam 52 just behind cross-pin 62 (see FIGS. 3, 4, 6a and 6b). The foot plate front support 36 is attachable by screws to the underside 20 of foot plate 16 by attachment to front attachment holes 22. The foot plate 16 is attachable at the heel area 32 with screws (not shown) to the rear foot plate support 38, that is located at the rear portion of the beam 52, in front of the rear beam support 46 connector. The rear foot plate support 38 spans the interior of the beam 52 and rotates around third cross-pin 82 that passes through rear foot plate support 38, allowing slight rotation of rear foot plate support 38 around third cross-pin 82 in relation to beam 52.

The beam 52 fits partially into cavity 40 of the sole 26 so that approximately half of the height of the beam 52 extends above the upper surface 28 of sole 26, and the foot plate 16 is positioned above the upper surface 28 of the sole. Foot plate 16 rests on foot plate front support 36, and foot plate rear support 38, and remains suspended above the side I-beam rails 52a and 52b of beam 52. Slight lateral adjustment of the foot plate 16 in relation to beam 52 does not negate the transfer of body weight downward from the wearer's foot onto the foot plate 16, with associated forces transmitted directly downward onto the horizontal length of the beam 52 through front support 36 and rear support 38.

The force sensing unit 50 includes a beam 52 extending from the heel area 32 to the forefoot area 34 underneath the foot plate 16, with the beam 52 insertable into the cavity 40 in the upper surface 28 of the sole 26 (see FIG. 1). The beam includes two rigid I-shaped side rails 52a, 52b forming approximately parallel sides of a front half frame 54 and rear half frame 74. The side rails are not continuous along the full length of the beam 52, since both side rails 52a, 52b include a notch 68, 72 respectively at the midpoint of each rail 68, 72 (see FIGS. 3 and 4). The beam 52 includes a central, rigid midpoint area that is composed of a forefoot central cross-member 58 and a rear central cross-member 78, providing structural rigidity to the midpoint area of the beam 52. The beam must be rigid across the entire length to negate undue deformation along the beam from horizontal forces created during walking movements, to allow clearance of the lower surface of the beam from contact with the interior surfaces of the cavity 40, and to assist efficient transfer of forces from the foot plate 16 to the central portion of the beam 52 from forces received at front support 36 and rear support 38.

When partial weight is applied anywhere along the length of footplate 16, there is a resulting small deflection of foot plate 16 about its instant center of rotation, namely cross-pin 82 enclosed in foot plate rear support 38. The front end of foot plate 16 is supported by foot plate front support 36, which contains a horizontally slotted opening to contain cross-pin 64. The purpose of the slot in front support 36 is to permit slight movement of cross-pin 64 with respect to front support 36 due to flexing of the beam 52, and the slight movement of the ends of foot plate 16 toward each other, as the ends and/or central area of the foot plate 16 are deflected down or up by placement of a large force onto the central area of the foot plate 16. The partial weight imposed by a wearer upon foot plate 16, is transferred to the beam 52 through cross-pins 64 and 82, resulting in a small deflection of beam 52. Beam 52 can deflect about its instant center of rotation, namely at cross-pin 84, contained within rear beam support connector 46. The front end of beam 52 is supported by cross-pin 62 enclosed within horizontally slotted opening 44 in front beam support connector 42. The purpose of the slot 44 is to permit slight movement of cross-pin 62 with respect to beam support connector 42, due to the slight bending of beam 52 under an imposed load by the wearer onto foot plate 16.

The front half frame 54 may include an open section into which battery packs, electrical component boards and/or electronic transmitters (not shown) can be attached. The front half frame 54 includes a forefoot open section 56 that includes a forefoot central cross-member 58 that extends across the central area of the beam and between side rails 52a, 52b (see FIG. 9). The forefoot central cross-member 58 forms a central, rigid bridge between the side rails 52a, 52b of the front half frame 54. A front cross-member 60 provides rigidity to the front half frame 54 of the rails 52a, 52b. The front half frame 54 is located underneath the forefoot portion 34 of the foot plate 16. In front of the front cross-member 60 is at least two beam pins spanning the width between the beam 54. The forward or first beam pin 62 can be positionable within the rearward facing slot 44 of the front beam support 42 connector, to provide a slidable interface for the first beam pin 62 to slide forward and rearward a very small amount of approximately 0.001 inches. The slidable interface allows the rigid rails 52a, 52b to shift slightly forward and rearward as a wearer walks while wearing the force monitoring shoe 10.

The rear half frame 74 includes a rear central cross-member 78 that abuts the forefoot central cross-member 58. Rear central cross-member 78 extends across the central area of the beam and between side rails 52a, 52b (see FIG. 9). The rear half frame 74 of beam 52 is bounded on the sides by the rails 52a, 52b, and rear cross-member 80 which is located underneath the heel portion 32 of the foot plate 16. Behind the rear cross-member 80 are at least two proximal beam pins spanning the distance between the sides of the frame 54. The third beam pin 82 is located rearward of the rear cross-member 80, and the fourth beam pin 84 is located rearward of the third beam pin 82. The fourth beam pin 84 is insertable through the bore 48 of the rear beam support 46, allowing the rear beam support 46 to rotate freely around the fourth beam pin 84. A rear portion of the rear beam support 46 is connectable to the rear end of the cavity 40, for support of the beam 52 within the cavity 40.

Figures 3, 4:
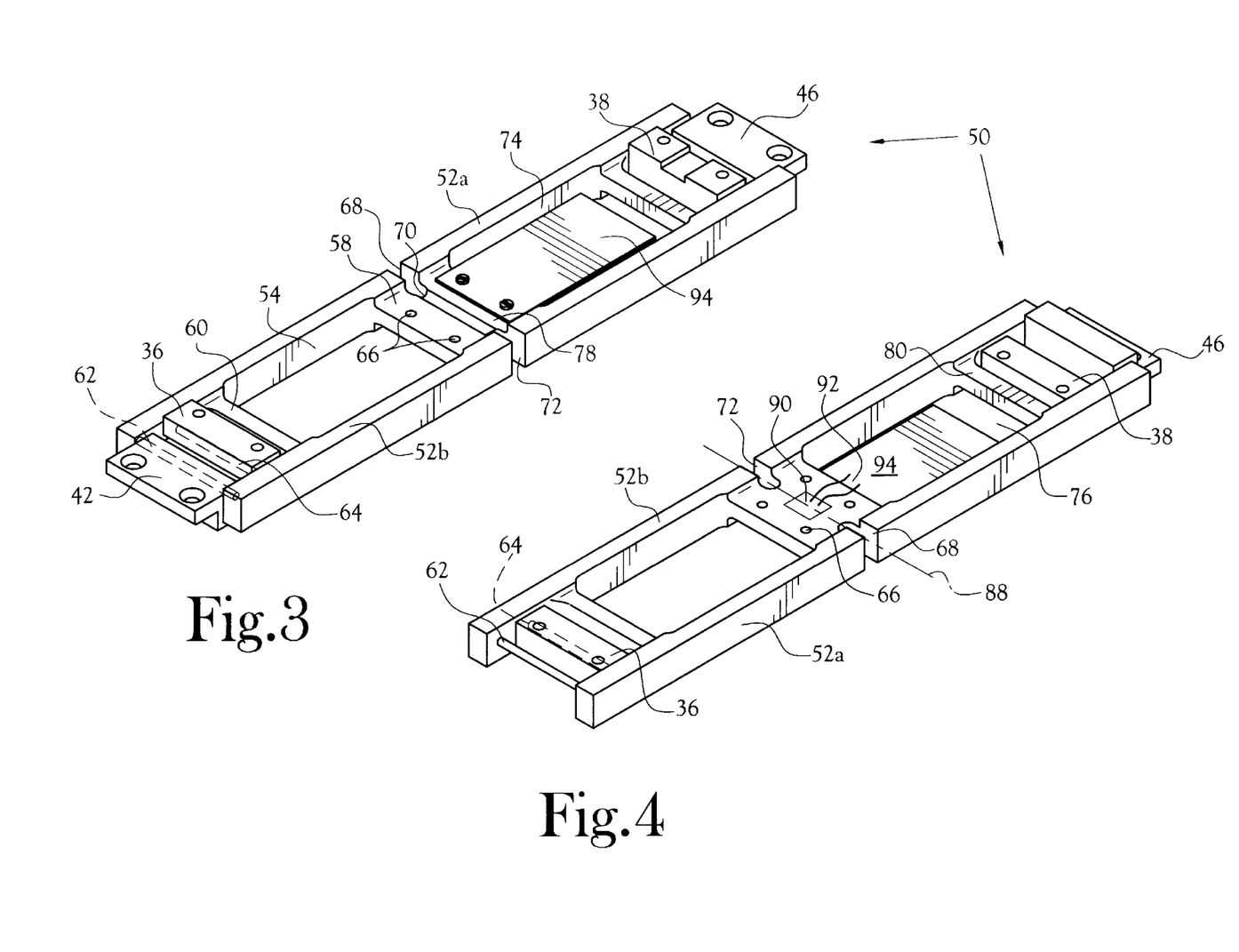
FIG. 3 is a top perspective view of a force sensing unit illustrating a central groove at the midpoint of the force sensing unit.
FIG. 4 is a bottom perspective view of FIG. 3 illustrating positioning of a strain gage at the centering axis of the force sensing unit.
Figures 5A, 5B, 6A, 6B, 7A, 7B, 8A, 8B:
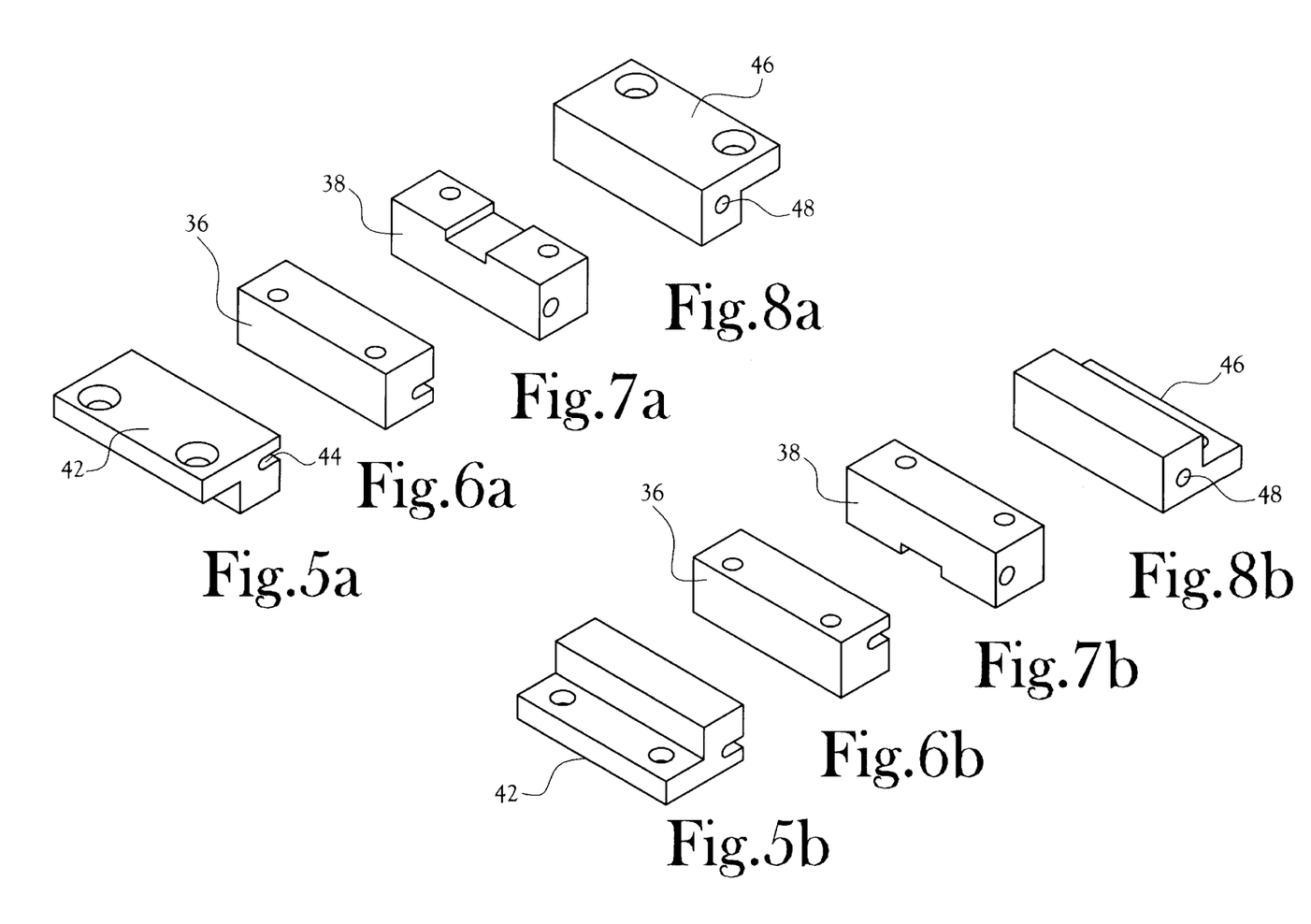
Figure 9:
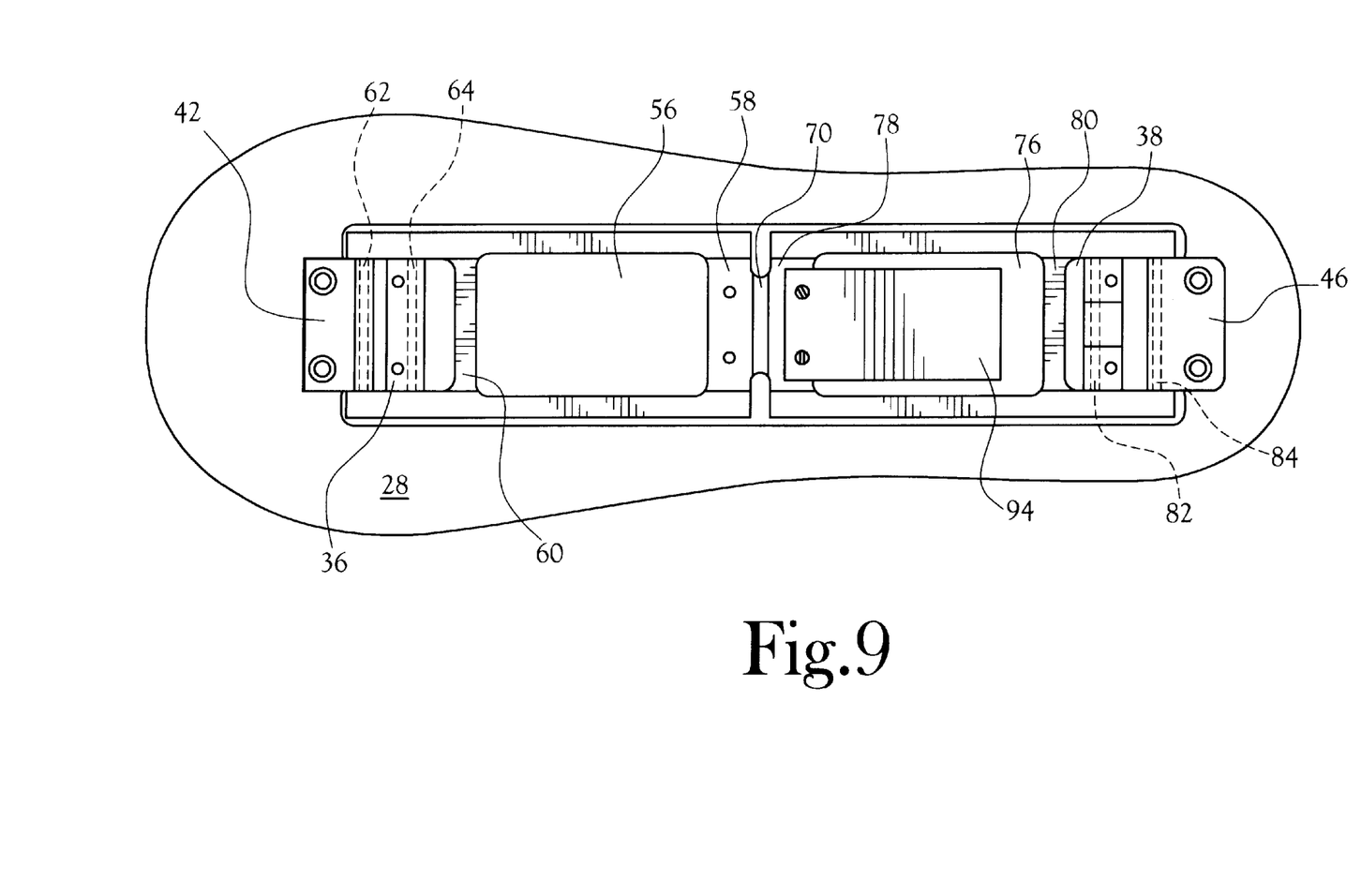
FIG. 9 is a top view of the assembled force sensing unit within a cavity of the force monitoring shoe sole.

At the central interface of the front half frame 54, and the rear half frame 74, is a central groove 70 that is positioned at preferably the midpoint of the beam 52 (see FIG. 3, 9, and 10). The center of the central groove 70 is preferably the same pre-selected distance ($X_2$) from the second cross-pin 64, slidably fitted through the foot plate front support 36, as the distance ($X_1$) from the third cross-pin 82, fitted through the rear support 38. The distance between first cross-pin 62 and second cross-pin 64 is approximately equal to the distance between the third cross-pin 82 and fourth cross-pin 84, therefore the center of the groove 70 is also preferably equidistant from the first cross-pin 62 and the fourth cross-pin 84. The location of the central groove 70 in the upper surface of the central cross-members 58, 78 of the beam 52 is important for proper measuring of the weight transmitted from the wearer's foot onto the foot plate 16. Below the central groove 70 on the lower side of the junction of central cross-members 58, 78, is at least one micro-sized strain gage 90 having strain measuring filaments that are oriented to measure strain across a centering axis 88 of the lower surface below the central groove 70. In a preferred embodiment, at least four strain gages are utilized in a bridge transducer orientation. At least two of the strain gages are oriented to be centered under the centering axis 88, with two additional strain gages oriented in close proximity to the centered strain gages. The two additional strain gages can be utilized for calibration by the electronic module 94 having an analyzing means 100 therein, during temperature changes affecting the beam 52.

Referring to FIG. 10, the weight Fw applied vertically downward by the wearer is converted to forces applied within the beam 52 by force component $F_1$ of weight $F_w$, exerted by the user's heel bearing upon foot plate 16, foot plate rear support 38, and cross-pin 82, and onto beam 52, thus creating a clockwise moment defined by $F_1$ multiplied by distance $X_3$ about cross-pin 84, which is the center of rotation for rear half frame 74. Likewise, the user's forefoot creates force component $F_2$ of weight $F_w$ upon foot plate 16, foot plate front support 36, and cross-pin 64, and onto beam 52, thus creating counter-clockwise moment defined by $F_2$ multiplied by distance $X_4$ about cross-pin 62, which is the sliding center of rotation for front half frame 54. To satisfy the laws of static equilibrium, the aforementioned clockwise moment at cross-pin 84 ($F_1$ multiplied by $X_3$) is offset by counter-clockwise moment at cross-pin 84 [$F_4$ multiplied by $(X_1+X_2+X_3+X_4)$], and the counter-clockwise moment at cross-pin 62 ($F_2$ multiplied by $X_4$) is offset by clockwise moment at cross-pin 62 [$F_3$ multiplied by $(X_1+X_2+X_3+X_4)$]. The above conditions apply regardless of the stiffness of the beam 52. The force and moment calculation principles apply regardless of where the force $F_w$ is placed on the foot plate 16 by the user's foot.

Bending moments generated by forces $F_1$ and $F_2$ produce a downward deflection and consequent stresses in the beam 52. The object of the beam design is for the deflection of the beam 52 to produce an amount of tensile stress at the lower surface of beam 52 at the centering axis 88 that will cause a strain which can be measured by the strain gage 90 operating within its normal range. To maximize sensing sensitivity, the depth of the central groove 70 is designed to result in the stiffness of the beam 52 to be much less at the central groove 70 than in the remainder of the beam. Consistent accurate signal output requires that distance $X_1$ equals distance $X_2$, and distance $X_3$ equals $X_4$, so that the calculated bending moment at the strain gage 90 is the same, regardless of where along the foot plate 16 the weight is applied.

Figure 11:
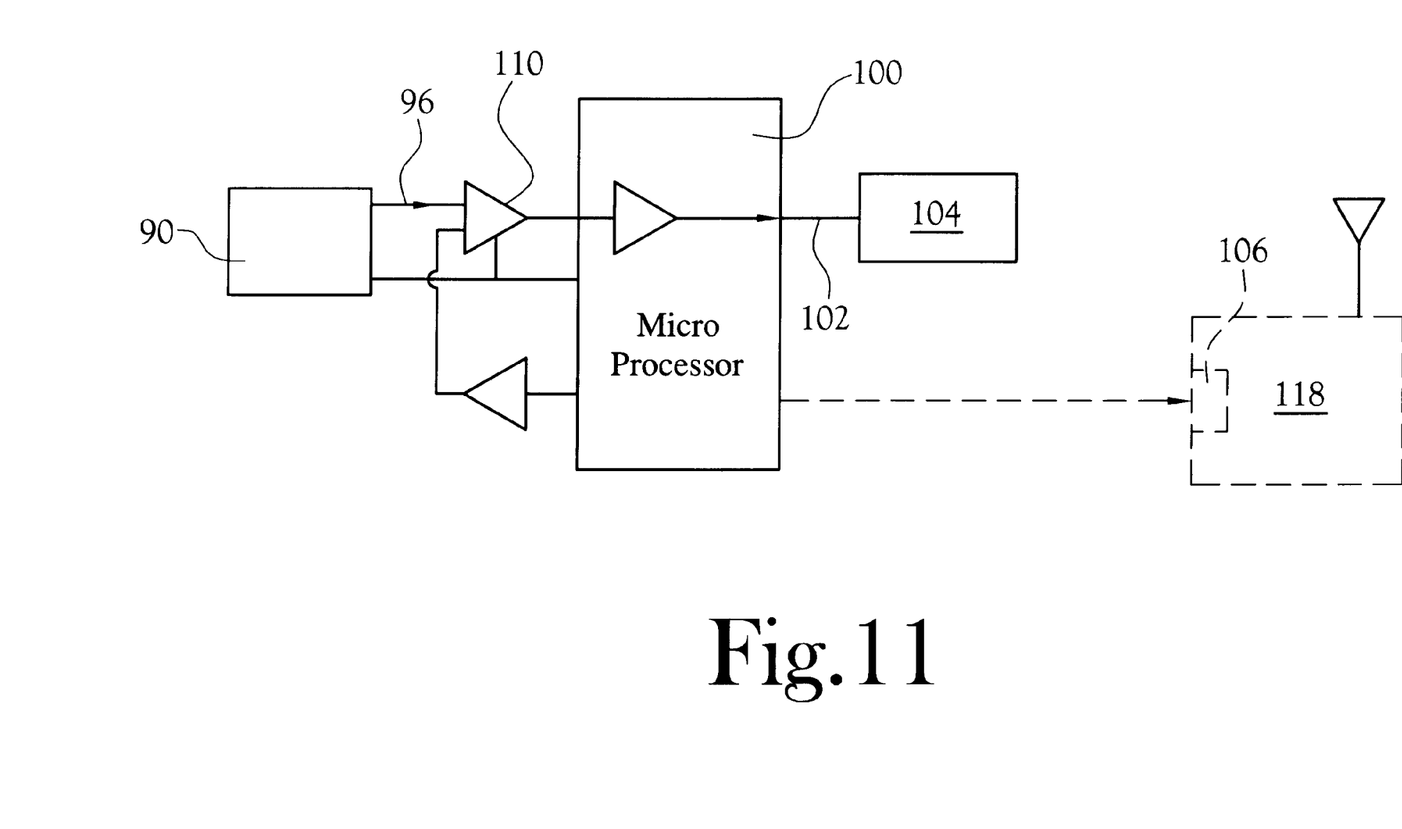
FIG. 11 is a diagram of the strain gage, microprocessor, and supporting electrical components of the force sensing and transmitter unit.

The strain gage 90 is connected by electrical connections 92 to a support platform with an electronic module 94 thereon, having an analyzing means 100 as part of the electronic module (see FIG. 4 and 11). The analyzing means 100, specifically a circuit board including a microprocessor and associated circuitry, is attachable to the rear part of central cross-member 78. A power source 110 can be located nearby, in the forefoot open section 56, or in a battery pouch 116 mounted exterior of the force sensing unit 50, on the upper enclosure 12 (see FIG. 1). The strain gage 90 provides measurements of voltage changes, which are indicative of weights $F_1$ and $F_2$ transmitted onto the beam 52 from the foot plate 16.

The electronic means of the analyzing means 100 includes microprocessor having circuitry to analyze the strain gage signals 96 generated by at least one strain gage 90. One embodiment utilizes a microchip and microcontroller that provides sufficient computing power to accomplish the calculations required for analyzing the strain recorded by strain gages 90, and for calculating forces imposed on the foot plate 16 by the wearer, along with additional software for completion of the multiple tasks such as analog to digital conversion of electrical signals. The microcontroller tasks include: a main program loop for periodic collecting of data from the strain gage 90 in a reading mode; mathematical analysis of strain gage voltage data to determine if the weight applied to the foot plate 16, and the resultant forces exerted on the beam 52 of the force sensing unit 50, exceeds the starting point in displaying force in pounds (a programmable minimum threshold for continued reading mode operation); computation of internal calibration information including analog output curves for strain gage signals 96; analog to digital conversion of strain gage signals 96; and watchdog timer functions for maintaining the microcontroller in reading mode versus sleep mode. The microcontroller is programmed in normal operations to conserve power by assuming a sleep mode, if previous readings by the strain gage did not exceed the minimum threshold weight value. A watchdog timer circuit within the microprocessor determines the periodic time increments that the microcontroller is awakened from sleep mode, for comparisons of the last reported weight measurements by the strain gage with the minimum threshold weight value. If weight values have not been received by the microcontroller that exceed the minimum threshold weight value, the microcontroller returns to sleep mode.

The microcontroller and the analog to digital converter of the microprocessor of analyzing means 100, converts strain gage signals 96 from analog to digital output signals 102, for transmittal of output signals 102 by transmitter 104 to the receiver unit circuitry 106. The first microprocessor may be connected by electrical wires through a slot 114 in foot plate 16 (see FIG. 2), for connection to calibration equipment for modifications to software and testing of the microcontroller and analog to digital converter (not shown).

Figure 12:
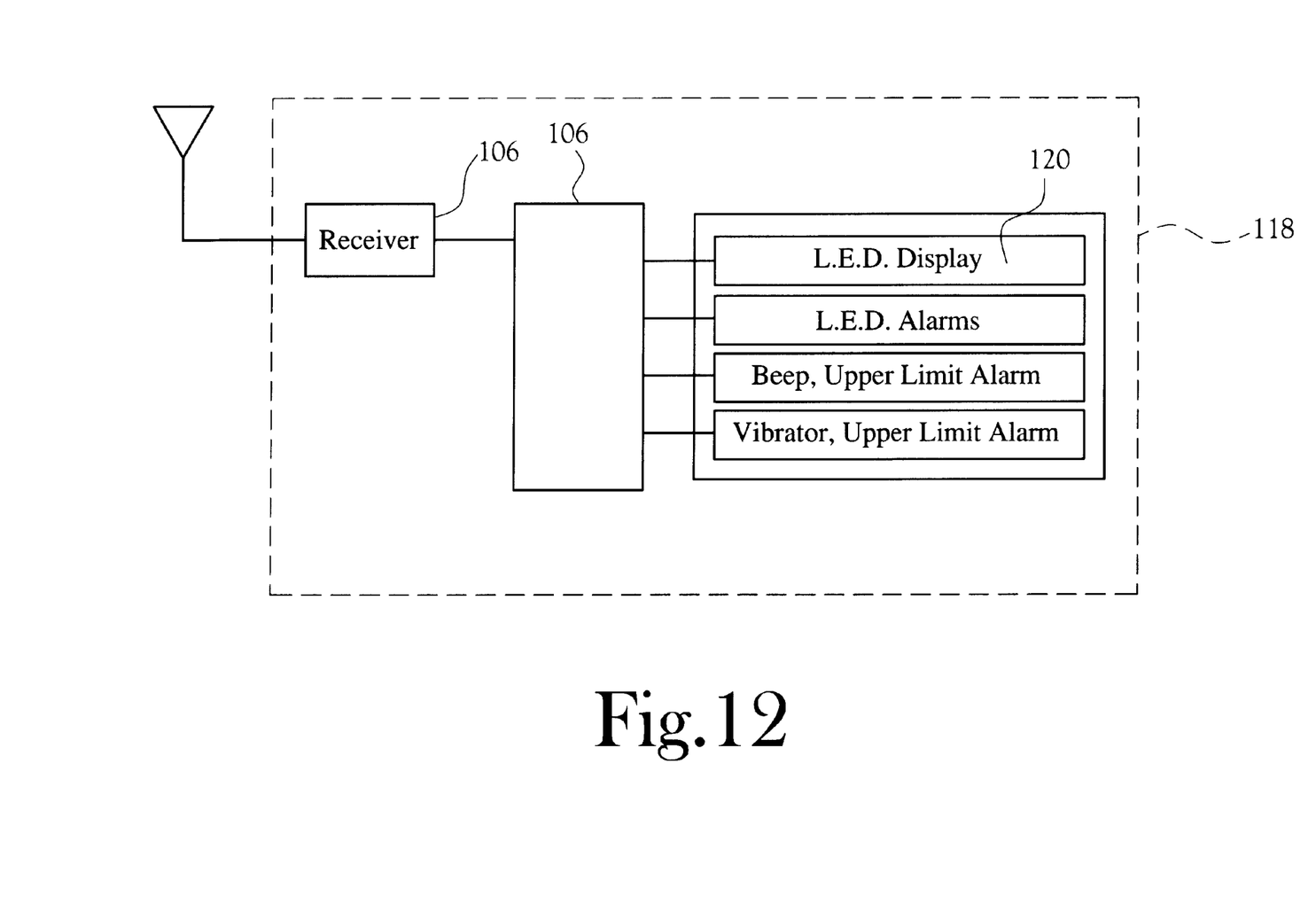
FIG. 12 is a diagram of the receiver and display unit of the present invention.

Analyses as to whether the output signals 102 have exceeded pre-selected upper threshold limits, or are below pre-selected lower threshold limits for minimum required weight placed on the foot, are accomplished in the receiver and display unit 118, which can be a device in the shape of a pager 118 (FIG. 1). The transmitted output signals 102 from the transmitter 104 of the force sensing unit 50, are received by a receiver unit circuitry having signal processing means 106 within the receiver and display unit 118, for comparisons of weight measurements with pre-selected upper threshold and lower threshold weight limits by appropriate software and computations of the processing means.

The receiver and display unit 118 can provide audible warnings in the form of alarms or variable volume controlled audio tones, and/or visual displays in the form of colored LED display 120 and a numerical display 124, and/or vibrator action of the pager shaped device to allow for notification of the wearer that preset weight limits have been exceeded for upper threshold limits. The colored LED display 120 can indicate by show of colored lights whether the lower threshold limits are met by the wearer of the force monitoring shoe 10. The receiver and display unit 118 can be programmed to display numerically the weights measured by the force sensing unit 50, and can be programmed by a wearer of the shoe 10 to readjust the upper threshold or lower threshold weight limits during rehabilitation therapy, or can be set manually to alternate upper threshold or lower threshold weight limits. The signal processing means 106 can be provided with adequate computer memory to allow storage of a certain number of prior weight readings over a series of steps, and to allow counting and storage of the number of steps taken by the wearer along with weights recorded for each step, for calculation of weights imposed above or below threshold levels by the wearer on the limb undergoing rehabilitation. The mode of the audible, light, or vibration signals can be selected individually by the wearer.

Upon notification to the wearer by the receiver and display unit 118, that weights imposed on the limb undergoing rehabilitation have exceeded the upper threshold limits or remained below the lower threshold limits, the wearer of the force monitoring shoe 10 can adjust his or her's gait to lessen the weight placed on the wearer's foot, or to increase the weight placed on the foot to allow continued, proper rehabilitation of the appropriate limb. The information gathered by the receiver and display unit 118 can be transmitted to a remote computer database and associated software for storage and calculations of the wearer's history of weight transfer onto the limb undergoing rehabilitation, for displaying real-time on a computer monitor, and for training of the wearer to improve the wearer's weight transfer on the limb undergoing rehabilitation.

ALTERNATIVE EMBODIMENTS

The above described force monitoring shoe 10 includes an alternate embodiment of a force sensing unit 50 including a beam 52 having dual "I" beams 52a, 52b of various widths, with at least two strain gages located at the centering axis 88, and up to four or more strain gages located in paired fashion on either side of the centering axis 88. The microprocessor of analyzing means 100 can provide analyses and averaging of measurements from the multiple strain gages to compute the actual forces applied by the wearer's foot onto the foot plate 16 and transmitted to the beam 52. When the strain gages are placed at the centering axis 88, underneath the central groove 70, then the strain gages and microprocessor can be calibrated to report accurate stress/strain readings relative to bending moments of various widths of "I" beams.

An alternate embodiment of the force sensing unit 50 can include a beam that includes non-parallel rails 52a and 52b, with rails decreasing to a lesser width at the front end of the beam (not shown), or decreasing to a lesser width at the rear end of the beam (not shown). With a decreasing width at the front end, the central groove 70' may be located slightly toward the rear of the centering axis 88'. With a decreasing width at the rear end, the central groove 70' and strain gage 90' may be located slightly toward the front of the centering axis 88'. Other configurations of the beam are possible, such as tapering of the thickness of each rail 52a and 52b from the rear to the front, with associated modifications to the positioning of the central groove 70' and strain gage 90'. Calibration of the strain gage to monitor the actual weight F placed on the foot plate 16 becomes more complicated as the strain gage is moved away from the centering axis 88 of a beam 52 that does not have symmetric proportions across the length and width of the beam.

Another alternate embodiment is a self-enclosed force sensing unit, in a slim footprint sized enclosure (not shown), that is insertable into an oversized shoe that a wearer obtains for use during the wearer's rehabilitation of a lower extremity. The self-enclosed force sensing unit includes the features described above and can contain a miniature transmitter located within front half frame 54 for transmitting the information processed by the microprocessor of analyzing means 100 to a display unit 118 that is attachable to a person's belt or clothing. The display unit 118 can alert the wearer by audible alarms, LED display 120, or vibrator motion that an upper threshold limit is exceeded, or a lower threshold limit is not achieved by the wearer. The display unit 118 can include mode selection buttons 122 for user adjustments.

Another alternate embodiment is a force sensing unit that is modified to fit an upper extremity such as on a hand or onto an elbow to provide therapeutic treatment during scapular stabilization exercises and general strengthening of upper extremities for improved weight support. The upper enclosure and foot/force plate of the force sensing unit can be modified to fit around a hand, and/or a forearm. Two similarly modified force sensing units can be attached onto both hands, forearms, and/or elbows for sensing of the forces placed on each force sensing unit during transfer exercises to train patients attempting to strengthen upper extremities. The shape of the force sensing unit upper enclosure, force plate, and associated force sensing beam can be appropriately modified by one skilled in the art to monitor force transferred from a hand, forearm, and/or elbow. Additional applications include sensing of forces generated during treatment of extremities experiencing neurological dysfunction from disuse, and for treatment of reflex sympathetic dystrophy of extremities.

A method of operation of the force monitoring shoe, including the steps of repetitive analyses of forces during steps with alarms provided to a wearer, is disclosed herein. While a preferred embodiment is shown and described, it will be understood that it is not intended to limit the disclosure, but rather it is intended to cover all modifications and alternate methods falling within the spirit and scope of the invention as defined in the appended claims. One skilled in the art will recognize variations and associated alternative embodiments upon review of the figures and the above specification. The foregoing description is exemplary in nature and the spirit and scope of the appended claims should not be limited to the description of the embodiment of the invention contained herein.

What is claimed is:

1. An apparatus for measuring force applied by the weight of a wearer onto a foot of the wearer, said apparatus providing an indication to the wearer when the force is below, or exceeds pre-selected limits, said apparatus comprising:

a body member for attachment to the foot of the wearer, said body member to support at least a portion of the foot, said body member including an upper enclosure, said upper enclosure having an attachment means for contact of said upper enclosure with the sides and top of the foot;

a foot plate removably insertable within said body member, said foot plate having an upper support surface for contact with the bottom of the foot, and having an underside;

a lower sole portion positioned below said foot plate, said lower sole portion having an upper surface, and a lower surface for contact with the support surface;

a cavity within said upper surface of said lower sole portion, said cavity having a front end and a rear end;

a force sensing unit having ends attachable within said cavity, said force sensing unit connectable to said underside of said foot plate, said force sensing unit measures strain in proportion to the force received by said force sensing unit from the foot in contact with said foot plate, said force sensing unit generates strain signals;

an electronic means mounted within said cavity, said electronic means is electrically connected to said force sensing unit, said electronic means receives said strain signals from said force sensing unit and converts said strain signals to output signals for transmission to one or more remote locations;

a power supply connectable to said electronic means;

a signal processing means at a remote location, said signal processing means receives said output signals from said electronic means; and a display unit coupled with said signal processing means, said display unit displays output signals from said signal processing means;

whereby force placed by the weight of the wearer of said body member onto said foot plate is transmitted through said foot plate to said force sensing unit attachable within said cavity, the force imparts strain on said force sensing unit which is measured as strain signals, said electronic means receives strain signals from said force sensing unit and converts said strain signals to output signals for radio transmission to said signal processing means for indication to the wearer when the force is below or exceeds pre-selected limits.

2. The apparatus of claim 1, wherein said force sensing unit comprises:

at least one beam positioned within said cavity, said beam having a generally rectangular shape, said beam having a forward end slidably supported at said front end of said cavity, and said beam having a rearward end rotatably connected at said rear end of said cavity;

a pair of side rails of said beam, said side rails forming the sides of said generally rectangular shape, said side rails parallel to each other;

a plurality of cross-pins that extend between said side rails of said beam;

a central cross-member of said plurality of cross-members, said central cross-member having a midpoint bridge between said side rails, said central cross-member having an upper surface and a lower surface, said upper surface having a central groove therein, said central groove is perpendicular to the major axis of said beam, said lower surface having a centering axis thereon, said centering axis located at about the midpoint of said beam;

at least one strain gage mounted on said lower surface of said central cross-member, said strain gage produces strain signals in proportion to the force received by said beam, said at least one strain gage mounted at said centering axis at about the midpoint of said beam;

an energizing voltage from a power source, said voltage connectable by electronic wiring to said strain gage and said electronic means; and at least one output lead, said output lead connecting between said strain gage and said electronic means.

3. The apparatus of claim 2, wherein said plurality of cross-pins further comprises a first pair and a second pair of cross-pins parallel to each other and perpendicular to the major axis of said beam, said cross-pins span said beam between said side rails, said first pair of cross-pins including a first cross-pin located near said forward end of said beam, said first pair of cross-pins including a second cross-pin located rearward of said first cross-pin, said second cross-pin located a pre-selected distance forward from said groove in said central cross-member, said second pair of cross-pins including a third cross-pin located said pre-selected selected distance rearward from said groove in said central cross-member, said second pair of cross-pins including a fourth cross-pin located near said rearward end of said beam, said first cross-pin including a front connector detachably attached to said front end of said cavity, said front connector slidably connectable to said first cross-pin, said second cross-pin including a front support connector detachably attached to said foot plate, said front support connector slidably connectable to said second cross-pin, said third cross-pin including a rotatable rear support connector detachably attached to said foot plate, and said fourth cross-pin including a rotatable rear connector detachably attached to said rear end of said cavity, whereby said foot plate receives forces transferred from the force applied from the foot of the wearer, the forces are transmitted through said front support connector and said second cross-pin, and through said rear support connector and third cross-pin onto said beam for detection of strain over the length of said beam by said strain gage at about the midpoint of said beam.

4. The apparatus of claim 3, wherein said beam includes one or more openings between said plurality of cross-members, said openings capable of containing said electronic means and said power supply.

5. The apparatus of claim 2, wherein said electronic means further comprises:

a microprocessor for analysis of said strain signals, said microprocessor converts said strain signals to output signals in radio frequency form; and a transmitter circuitry for transmission of output signals in radio frequency form from said microprocessor to said signal processing means at one or more remote locations.

6. The apparatus of claim 5, wherein said signal processing means receives said output signals from said transmitter circuitry, said signal processing means processes said output signals with a second microprocessor for analysis of output signals and notification of the wearer.

7. The apparatus of claim 6, wherein signal processing means further comprises a reporting means, said reporting means includes visual and audible alarms for notification of the wearer of said signal processing means, said alarms notify the wearer if a pre-selected upper threshold weight limit is exceeded, or notify the wearer if a lower threshold weight limit is not achieved.

8. The apparatus of claim 7, wherein said reporting means alarms further comprise a light display, a light display with vibration of said processing means, or a light display and an audible alarm for notification of the wearer if the pre-selected upper threshold weight limit is exceeded, or if the lower threshold weight limit is not achieved.

9. The apparatus of claim 8, wherein said reporting means alarms further comprise a numerical reading for display of output signals.

10. The apparatus of claim 9, wherein said second microprocessor for analysis of said output signals is programable for reset of analysis when the pre-selected upper threshold weight limit is exceeded, or for reset when the lower threshold weight limit is not achieved.

11. The apparatus of claim 10, wherein said second microprocessor is programable for reset to an alternative upper threshold limit below the pre-selected upper threshold weight limit, or for reset to an alternative lower threshold limit below the lower threshold weight limit, said alternative upper or lower threshold weight limit can be set manually by said wearer.

12. The apparatus of claim 11, wherein said reporting means can display a number for each force measured by said strain gage during each step by said wearer.

13. The apparatus of claim 1, wherein said body member and said foot plate can be selected from a plurality of sizes to fit the foot of the wearer.

14. A method of operation of a force monitoring system for measuring force applied to a foot by the weight of a wearer of the force monitoring system, comprising the steps of:

(a) providing an orthopedic shoe for enclosure of the foot of the wearer, said shoe having a foot plate and a sole with an interior cavity;

(b) inserting a beam into said sole cavity, said beam having at least one force measuring strain gage on said beam;

(c) connecting a microprocessor by electrical connectors to said at least one strain gage;

(d) attaching a transmitter by electrical connectors to said microprocessor, said transmitter transmitting signals in proportion to force measured by said strain gage;

(e) placing said orthopedic shoe on the wearer's foot;

(f) monitoring the force measured by said strain gage, said strain gage generating electronic signals in proportion to said force applied on said foot plate;

(g) analyzing said electrical signals generated by said monitoring step, said analyzing step generating output signals from said microprocessor;

(h) transmitting said output signals in the form of radio frequency signals to a receiver attachable to said wearer;

(i) processing said output signals in a signal processing means in a display unit at a remote location, said signal processing means receives said output signals from said transmitting step and compares said output signals to pre-selected upper threshold weight limits and lower threshold weight limits; and (j) displaying to the wearer said output signals if said signals are above the pre-selected maximum weight limits or are below the minimum weight limits.

15. The method of claim 14, wherein said step of analyzing further comprises:

(a) setting a desired range of measured force, said desired range including said pre-selected upper threshold weight limit, and said lower threshold weight limit;

(b) reporting output signals for measured forces outside said desired range of measured force, with no reporting of signals for measured forces below said upper threshold weight limits and above said lower threshold weight limits; and (c) generating analyzed output signals for transfer to said transmitting step.

16. The method of claim 15, wherein said step of displaying further comprises:

(a) receiving said analyzed output signals in the form of radio frequency signals at said receiver attachable to said wearer;

(b) signaling said received output signals in the form of a light display, a light display with vibration of said processing means, or a light and audible alarm for output signals for measured force outside said desired range;

(c) processing said received output signals as a numerical reading for measured force outside said desired range;

(d) counting the total steps taken by the wearer up to a predetermined step limit;

(e) storing in memory the total steps counted in said counting step; and (f) displaying said numerical readings and said counted total steps.

17. A force monitoring apparatus for measuring force applied by the weight of a wearer to a foot of the wearer of an orthopedic shoe, the apparatus providing an indication to the wearer when the force is below, or exceeds pre-selected limits, the apparatus comprising:

a base within the orthopedic shoe, said base having an upper sole layer that extends the length of the shoe, and having a lower sole surface for contact with the support surface;

a cavity within said upper sole layer, said cavity having a forefoot end and a heel end;

a foot plate that is attachable over said upper sole layer and said cavity, said foot plate being rigid;

a beam insertable into said cavity, said beam including two side rails, a midpoint cross-member having a midpoint bridge between said side rails, and at least two cross-members on opposite sides of said midpoint cross-member, said cross-members connected between the side rails forming a generally rectangular frame, said beam is connectable underneath said foot plate;

a strain gage positioned under said midpoint cross-member of said beam, said strain gage generates strain signals in proportion to the force placed by the foot of the wearer onto the foot plate;

an electronic processing means located proximal to said strain gage and connected within said side rails of said beam, said electronic processing means generates output signals in proportion to the strain signals generated by said strain gage;

a power supply connectable to said electronic processing means;

a transmitter of output signals from said electronic processing means, said transmitter connectable to the orthopedic shoe, said transmitter emits output signals in proportion to said output signals generated by said electronic processing means;

a receiver of output signals from said transmitter, said receiver located separate from the orthopedic shoe;

a signal processing means within said receiver, said signal processing means receives said output signals from said transmitter; said signal processing means generates alarm signals if said output signals are below, or exceed pre-selected limits; and a display unit coupled with said signal processing means, said display unit displays said alarm signals from said signal processing means;

whereby said beam flexes when the wearer places force onto said foot plate, with resultant output signals generated by said electronic processing means, with said output signals transmitted to said receiver of output signals from said transmitter, said receiver displays said alarm signal to notify wearer when the force is below, or exceeds pre-selected limits.

18. The force monitoring apparatus of claim 17, wherein said beam further comprises:

a forefoot section of said beam, said forefoot section having a generally rectangular shape, said forefoot section having a front end and a central cross-member end, said forefoot section including:
a front cross-member positioned near said front end of said forefoot section;
a second cross-member that spans said central cross-member end, said second cross-member forms part of the said midpoint cross-member having said strain gage underneath;
a first cross-pin that spans said front end of said forefoot section, said first cross-pin positioned in front of said front cross-member;
a second cross-pin that spans said front end of said forefoot section, said second cross-pin positioned between said first cross-pin and said front cross-member;
said second cross-pin positioned a pre-selected distance from said strain gage; and
a front beam support connector connectable to said first cross-pin, said front beam support connector is attachable by screws to said forefoot end of said cavity of the shoe;
a heel section of said beam, said heel section having a generally rectangular shape, said heel section having a heel central end and a rear end, said heel section including:
a first heel cross-member that spans said heel section, said first heel cross-member forms part of said midpoint cross-member having said strain gage underneath;
a second heel cross-member that spans a point near said rear end of said heel section;
a third cross-pin that spans said heel section distal said second heel cross-member from said midpoint cross-member, said third cross-pin positioned said pre-selected distance from said strain gage as said second cross-pin of said forefoot section;
a fourth cross-pin that spans said heel section at said rear end of said heel section, said fourth cross-pin distal said third cross-pin; and
a rear beam support connector rotatable around said fourth cross-pin, said rear beam support connector is attachable by screws to said heel end of said cavity of the shoe; and
a central groove at a mid-point of said midpoint cross-member, said central groove reduces the thickness of said mid-point of said midpoint cross-member, said central groove having said strain gage centered underneath;

whereby said beam is insertable into said cavity, said foot plate is placed over said beam and said cavity, said foot plate is attachable over said beam, with force transfer by the foot of the wearer during standing and walking provides variable forces on said foot plate, said strain gage generates strain signals proportional to the force placed on said foot plate.

19. The force monitoring apparatus of claim 18, wherein said electronic processing means further comprises:
a microprocessor connected to said strain gage, said microprocessor generates electrical signals in proportion to the strain signals generated by said strain gage;
a receiver of electrical signals from said strain gage, said receiver channels electrical signals to said electrical circuitry;
an electrical circuitry including electrical components for the analysis of electrical signals from said strain gage;
an analog to digital converter, for converting the electrical signals to output signals; and
a programable computer program including pre-selected upper threshold weight limits and lower threshold weight limits, said computer program reports output signals for measured weights outside said pre-selected upper threshold weight limits and lower threshold weight limits, with no reports of output signals for measured weights below said upper threshold weight limit but above said lower threshold weight limit.

20. The force monitoring apparatus of claim 19, wherein said receiver further comprises:
a receiver having a LED display and a microprocessor having storage memory;
a plurality of LED alarm signals stored in said microprocessor memory;
at least one alarm lower limit stored in said microprocessor memory;
at least one alarm upper limit stored in said microprocessor memory;
a vibrator mechanism triggered to vibrate at said upper threshold weight limit, and at said lower threshold weight limit; and
a calibration connection for external connection with a calibration computer.

* * * * *

UNITED STATES PATENT AND TRADEMARK OFFICE
CERTIFICATE OF CORRECTION

PATENT NO. : 6,122,846
DATED : September 26, 2000
INVENTOR(S) : Frank B. Gray, et al

It is certified that error appears in the above-identified patent and that said Letters Patent is hereby corrected as shown below:

Title Page, item [75] delete "Raimer" and insert -- Rainer --.

Signed and Sealed this

Fifteenth Day of May, 2001

Attest:

NICHOLAS P. GODICI

Attesting Officer    Acting Director of the United States Patent and Trademark Office